United States Patent
Lichtblau et al.

(10) Patent No.: US 8,409,556 B2
(45) Date of Patent: *Apr. 2, 2013

(54) TOPICAL FORMULATIONS FOR THE PREVENTION OF SEXUALLY TRANSMITTED DISEASE AND METHODS OF PRODUCING THE SAME

(75) Inventors: Craig Lichtblau, Jupiter, FL (US); Jose I. Iparraguirre, Miami, FL (US)

(73) Assignee: CLJI IP Company, LLC, North Palm Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/274,813

(22) Filed: Oct. 17, 2011

(65) Prior Publication Data

US 2012/0034311 A1    Feb. 9, 2012

Related U.S. Application Data

(63) Continuation of application No. 12/038,283, filed on Feb. 27, 2008, now Pat. No. 8,062,631, which is a continuation-in-part of application No. 11/536,035, filed on Sep. 28, 2006, now abandoned.

(51) Int. Cl.
  *A61K 31/74* (2006.01)
(52) U.S. Cl. .................................. 424/78.07
(58) Field of Classification Search ............... 424/78.07
  See application file for complete search history.

(56) References Cited

U.S. PATENT DOCUMENTS

| | | | |
|---|---|---|---|
| 4,952,411 A | 8/1990 | Fox, Jr. et al. | |
| 5,439,685 A | 8/1995 | Augros | |
| 6,183,762 B1 | 2/2001 | Deckers et al. | |
| 6,328,991 B1 | 12/2001 | Myhling | |
| 6,355,235 B1 | 3/2002 | Cone et al. | |
| 6,582,711 B1 | 6/2003 | Asmus et al. | |
| 6,656,928 B1 | 12/2003 | McCadden | |
| 6,667,026 B1 * | 12/2003 | Goldman et al. | 424/47 |
| 6,821,958 B1 | 11/2004 | Hershline | |
| 6,835,717 B2 | 12/2004 | Hildreth | |
| 7,097,828 B2 | 8/2006 | Meyer et al. | |
| 2003/0031727 A1 | 2/2003 | Hahn et al. | |
| 2003/0143189 A1 | 7/2003 | Askill et al. | |
| 2005/0048139 A1 | 3/2005 | Modak et al. | |
| 2006/0018937 A1 | 1/2006 | Friedman et al. | |

FOREIGN PATENT DOCUMENTS

EP       1506781       2/2005

OTHER PUBLICATIONS

Tennican, P, The Diverse effects of topical and systemic administration of zinc on the virulence of Herpes simplex genitalis, Life Sciences, vol. 24, No. 20, May 14, 1979.

Eby, G, Use of topical zinc to prevent recurrent herpes simplex infection: Review of literature and suggested protocols, Medical Hypotheses, vol. 17, No. 2, Jun. 1, 1985.

Database GNPD, Mintel; Sensitive Facial Skin Extra Protective Lotion, Apr. 2003, Database accession No. 10134434.

Skoler-Karpoff, S, Efficacy of Carraguard for prevention of HIV infection in women in South Africa: a rondomised, double-blind, placebo-controlled trial, The Lancet, Dec. 6, 2008.

Supplemental European Search Report issued in Applicant No. 08744462.6-2112/2257263 PCT/US2008058428 dated May 9, 2012.

\* cited by examiner

*Primary Examiner* — Benjamin Packard
(74) *Attorney, Agent, or Firm* — Ferris H. Lander

(57) ABSTRACT

The present invention is directed towards various topical protective formulations which may be used as an adjunct in preventing the spread of a broad range of sexually transmitted diseases. The product is intended to be used as a topical lotion, cream, emulsion, or the like. The film forming excipients and active ingredients in the following formulations have demonstrated unique skin protective barrier properties with enhanced persistence that inhibits transmission of sexually transmitted diseases.

13 Claims, No Drawings

TOPICAL FORMULATIONS FOR THE PREVENTION OF SEXUALLY TRANSMITTED DISEASE AND METHODS OF PRODUCING THE SAME

CROSS REFERENCE TO RELATED APPLICATION

This application is a continuation of application Ser. No. 12/038,283, filed Feb. 27, 2008, which is a continuation-in-part of application Ser. No. 11/536,035, filed on Sep. 28, 2006, and now abandoned, the contents of each of which are herein incorporated by reference.

FIELD OF THE INVENTION

This invention relates to topical protective formulations for use in the prevention of the spread of sexually transmitted diseases (STDs); and particularly to unique topical formulations including a plurality of film forming excipients which act in concert to provide a barrier to help inhibit the transmission of STDs.

BACKGROUND OF THE INVENTION

Sexually transmitted diseases (STDs) are a universal concern, effecting millions of individuals and straining health care systems. More than 20 different sexually transmitted diseases have been identified by the medical community and generally fall into two groups, including bacterial types (e.g., gonorrhea, chlamydia and syphilis) and viral types (human immunodeficiency virus (HIV), human papilloma virus (HPV) and hepatitis). The numerous diseases affect men, women and children of all backgrounds, races and economic classifications. Despite years of research and educational programs, the transmission of sexually transmitted diseases remains a global health threat. Although specific methods of transmission may vary depending on the disease-causing organism, STDs are usually transmitted to the uninfected person through injured or exposed skin or mucous membranes during sexual contact.

Treatments may be available for some types of STDs (e.g. antibiotic treatment for gonorrhea or chlamydia). However, most people who suffer from these types of STDs are unaware that they have the disease and therefore do not get the necessary treatment. Moreover, because of the sociological impact and generally negative stigma associated with these diseases, people are reluctant to seek such treatments. The continued emphasis on educating the population as to the use of "mechanical barriers" such as condoms has helped to decrease the morbidity of most STDs but more preventative methods need to be developed to prevent STD transmission.

Chemical actives such as microbicides, antimicrobials, and spermicides, most notably, nonylphenoxypoly(ethyleneoxy)-ethanol (also referred to as nonoxynol-9) have been used in topical formulations to effectively reduce the rate of STD transmission, especially when used in conjunction with prophylactics. However, many of these chemical actives are harsh and have been shown to induce local irritation, inflammation, and ulcerations which might actually favor the transmission of STDs. Thus, a need exists for topical formulations that do not cause irritation and will help inhibit the spread of STDs, especially when used in combination with condoms, and thereby provide an additional degree of protection from contamination, should the condom become damaged.

PRIOR ART

Although there are numerous patents and publications directed to formulations containing chemical actives, such as, microbicides, antimicrobials, spermicides, and drug delivery carriers (liposomes, micelles), none of the known prior art teach formulations comprising non-irritating agents that provide a physical barrier to the permeation of pathogens.

U.S. Patent Application 2003/0143189 A1 to Askill et al., is directed to a method of treating skin lesions by forming a polymeric film over the lesions to inhibit proliferation of infectious agents in the lesions. These compositions also include one or more chemical agents in combination therewith.

U.S. Pat. No. 6,835,717 to Hildreth discloses a method of reducing the risk of a sexually transmitted pathogen by contacting a pathogen within the composition which consists of β-cyclodextrin.

U.S. Pat. No. 6,821,958 to Hershline discloses a method of preventing viral transmission using an alkylsulfate derivative of sulfated dextrin as a topical formulation.

U.S. Pat. No. 6,582,711 to Asmus et al., discloses an antimicrobial hydroalcoholic composition having a cationic polymeric thickener.

U.S. Pat. No. 6,355,235 to Cone et al., consists of an antibody capable of trapping sperm and a pharmaceutical carrier.

U.S. Pat. No. 6,328,991 to Myhling discloses a chemical composition to prevent the transmission of sexually transmitted diseases comprising nonylphenoxpoly-(ethyleneoxy)-ethanol, benzalkonium chloride and povidone iodine.

U.S. Pat. No. 5,439,685 to Augros is a composition of an agent active against microorganisms responsible for sexually transmitted diseases together with a film forming agent such as dimethylpolysiloxane, and benzalkonium chloride as a spermicidal.

U.S. Pat. No. 4,952,411 to Fox, Jr. et al., is a composition of silver sulfadiazine, alone or in combination with chlorhexidine or sodium deoxycholate (antimicrobial and detergent).

SUMMARY OF THE INVENTION

The purpose of this invention is to provide non-irritating protective formulations to be used as an adjunct in preventing the spread of a broad range of sexually transmitted diseases. The products of the present invention can be formulated as a topical lotion, cream, solution, emulsion, or the like, and will be hereinafter referred to as creams The use of antimicrobial/antiviral active agents and film-forming excipients in the following formulations have demonstrated unique skin protective barrier properties with enhanced persistence that inhibit "skin to skin" and "sore to sore" transmission of pathogens (e.g., viruses, bacteria, fungi, parasites, ectoparasites and mycoplasmas) linked to communicable diseases.

Skin protectant products are regulated under CFR 21 Part 347 "Skin Protectant Drug Products for Over the Counter Human Use". The official description of a skin protectant is "a drug product that temporarily protects injured or exposed skin or mucous membrane surfaces from harmful or annoying stimuli, and may help provide relief to such surfaces." These regulations cover applicable ingredients, as well as labeling requirements for over the counter skin protectants. Active ingredients officially classified as skin protectants compositions as well as certain combinations of these compositions are listed in the CFR 21 Sec. 347.10, reproduced in Table 1 below. In accordance with the instant invention, the phrase "a skin protectant composition provided in a skin protecting effective concentration" will be understood to mean any of the following ingredients within their designated range of concentrations:

These include any of the following within the concentration range specified:

TABLE 1

| Ingredient | Concentration |
|---|---|
| Allantoin | 0.5 to 2.0% |
| Aluminum hydroxide gel | 0.15 to 5.0% |
| Calamine | 1.0 to 25.0% |
| Cocoa Butter | 50.0 to 100.0% |
| Cod liver oil | 5.0 to 13.56% (in accordance with Sec. 347.20 (a) (1) or (a) (2), provided the product is labeled so that the quantity used in a 24-hr period does not exceed 10,000 USP Units vitamin A and 400 USP Units cholecalciferol. |
| Colloidal oatmeal | 0.007 minimum; 0.003 minimum in combination with mineral oil in accordance with Sec. 347.20 (a) (4). |
| Dimethicone | 1.0 to 30.0% |
| Glycerin | 20.0 to 45.0% |
| Hard fat | 50.0 to 100.0% |
| Kaolin | 4.0 to 20.0% |
| Lanolin | 12.5 to 50.0% |
| Mineral oil | 50.0 to 100.0%; 30.0 to 35.0% in combination with colloidal oatmeal in accordance with Sec. 347.20 (a) (4). |
| Petrolatum | 30.0 to 100.0% |
| Topical starch | 10.0 to 98.0% |
| White petrolatum | 30.0 to 100.0% |
| Zinc acetate | 0.1 to 2.0% |
| Zinc carbonate | 0.2 to 2.0% |
| Zinc oxide | 1.0 to 25.0% |

It has been discovered that incorporation of at least one of the aforementioned skin protectants compositions listed in Table 1 in combination with other film forming excipients, in particular, film-forming emollients (e.g., Cetostearyl alcohol, Cetyl alcohol), silicone-containing excipients/skin protectants (e.g., polydimethylsiloxane derivatives of varying viscosities, utilized either singly or in combination, and marketed under names such as Dimethicone 20 and Dimethicone 12500), emulsifying agents (e.g. selected from Cetearyl alcohol (a mixture of fatty alcohols, predominantly stearyl and cetyl alcohols, polyoxyethylene ethers of a mixture of high molecular mass saturated fatty acids (mainly cetyl alcohol and stearyl alcohol, having a number of ethylene oxide residues in the polyoxyethylene chain, e.g. 20, 12 or the like, and referred to as Ceteareth-20, Ceteareth-12, or the like, and/or mixtures thereof), humectants (e.g. glycerin and anhydrous lanolin) and chelating compounds (e.g. disodium edetate) in a formulation for topical application results in a product that temporarily protects injured or exposed skin or mucous membrane surfaces from harmful or annoying stimuli, thereby preventing cross-contamination of pathogenic microorganisms responsible for sexually transmitted diseases (e.g., Herpes simplex virus type 1 and type 2 (HSV-1, HSV-2), human immunodeficiency virus (HIV), or the like) through skin or mucous membrane surfaces. In addition to the hydrophobic, barrier-forming formulation, active agents that prevent bacterial or viral transmission are also included. The novel formulation products of this invention are persistent in that they form a film or barrier on healthy or even damaged skin.

The hydrophobic portions of the instant formulations utilize a combination of film-forming excipients, including skin protectant(s) listed in Table 1, silicones and silicone derivatives or like equivalents, and film-forming emollients. These ingredients are dispersed by the emulsifiers throughout the continuous aqueous phase. They liquify and spread over the skin as a result of exposure to body heat. This forms a physical hydrophobic layer which resides on the skin surface (including mucosal membranes) and provides a barrier which would inhibit penetration of liquids and pathogens which are primarily hydrophilic in nature. When used in combination with consistent and careful use of condoms, the products of the present invention help inhibit the spread of STDs and protect the skin from contamination should the condom become damaged.

Accordingly, it is an objective of the instant invention to teach various topical protective formulations to be used in preventing the spread of a broad range of sexually transmitted diseases.

Another objective of the present invention is to teach formulations which are condom compatible, meaning that they are latex friendly and provide effective lubricity.

It is yet another objective of the instant invention to teach skin protective formulations wherein contact with the skin results in the formation of a hydrophobic skin protective surface layer.

It is yet another objective of the instant invention to teach skin protective formulations wherein contact with the skin results in the formation of a mechanical barrier skin protective surface layer.

It is yet another objective of the instant invention to teach skin protective formulations wherein contact with the skin results in the formation of a hydrophobic skin protective surface layer containing antiviral/antimicrobial agents.

Yet another objective of the invention is to teach products formulated as a lotion, cream, solution, emulsion, or other topically applied product.

Other objects and advantages of this invention will become apparent from the following description, wherein are set forth, by way of illustration and example, certain embodiments of this invention.

DETAILED DESCRIPTION OF THE INVENTION

Detailed embodiments of the instant invention are disclosed herein, however, it is to be understood that the disclosed embodiments are merely exemplary of the invention, which may be embodied in various forms. Therefore, specific functional and structural details disclosed herein are not to be interpreted as limiting, but merely as a basis for the claims and as a representation basis for teaching one skilled in the art to variously employ the present invention in virtually any appropriately detailed structure.

Zinc oxide is an inert, non toxic chemical compound with the chemical formula of ZnO. Zinc Oxide can be used as a skin barrier. When applied to skin, Zinc Oxide acts as a mechanical barrier that physically excludes isolates and prevents the skin from any contact with harmful stimuli. Zinc Oxide is often used in creams or lotions and provides a continuous barrier which also helps prevent the loss of active ingredients due to friction and rubbing. Because of its inert, non-toxic characteristics and general non-solubility in water, it can be applied to skin as many times as may be needed. While zinc oxide is the preferred skin protectant composition of the present invention, other suitable skin protectant compositions and their amounts effective to provide skin protection as listed in Table 1 above could be used herein (e.g., Dimethicone).

Glycerin (INCI name: Glycerin) is a non-irritating humectant and film former. It is also water soluble. Moreover, glycerin is compatible with latex products and provides extended lubricity, which makes it a common base for many products designed for genital use.

Lanolin is a humectant isolated from wool-bearing animals such as sheep. It is a product of the sebaceous gland and consists mostly of a mixture of cholesterol and the esters of several fatty acids. It has many commercial uses, including within the medical and cosmetic industries.

Benzalkonium Chloride is a member of the quaternary ammonium compounds. These compounds are a group of ammonium salts in which organic radicals have been substituted for all four hydrogens of the original ammonium cation. Benzalkonium Chloride has been reported to be an effective anti-viral wetting agent in the prevention of transmission of viral diseases such as HIV and herpes simplex virus. Benzalkonium Chloride is also listed in the FDA Topical Antimicrobial Drug Products Monograph as a First Aid Antiseptic. Although the use of Benzalkonium Chloride is preferred, it is contemplated that any other quaternary ammonium salt compound could be used without departing from the scope of the present invention, such as CETRIMIDE (alkyltrimethylammonium bromide).

The phase "film-forming emollient" refers to any excipient suitable for cosmetic and pharmaceutical applications which forms a water-repelling film. According to a preferred, albeit non-limiting embodiment, the film-forming emollients are cetyl alcohol and cetostearyl alcohol. Cetyl alcohol (IUPAC name of 1-hexadecanol) is a member of the alcohol class of compounds. It is a solid organic compound and belongs to a group of fatty alcohols. In addition to its use as an emollient, it is often used in the cosmetic industry as a surfactant in shampoos, emulsifiers or thickening agents in the manufacture of skin creams and lotions. Cetostearyl alcohol is a blend of cetyl alcohol and stearyl alcohol, two fatty alcohols derived from vegetable sources.

The phase "silicone-containing excipient" refers to any silicone or silicone derivatives, including silicone-based skin protectants, suitable for cosmetic and pharmaceutical applications which acts as an emollient and forms a water-repelling film, including silicone oils. In addition to skin barriers, silicone and silicone oils are highly substantive on the skin. As a result of this property, silicon and silicone oils are often used in topical formulations, such as creams and lotions, to improve the substantivity of active ingredients on the skin.

After applying the topical formulations to the skin and removing volatile substances, the film formed as a result of using a silicone-containing excipient helps to maintain the active ingredient in close contact with the skin and prevents the loss of the active ingredient by abrasion. The ability to form hydrophobic films which can easily be applied and spread over skin accounts for high resistance to wash-off and rub-off. Use of silicones in topical formulations over petroleum-based products is more desirable because silicones do not exhibit the negative aesthetics of petroleum and, unlike petroleum, are known to be compatible with the materials used to manufacture condoms. According to one non-limiting embodiment, Dimethicone (preferably Dimethicone 20 cSt and Dimethicone 12500 cSt) is preferred. Dimethicone is a highly pure, non-volatile silicone fluid which is colorless and odorless. It can be used as a lubricant and emollient skin protectant.

Ceteareth-12 is part of a family with the INCI name of Ceteareth-n and refers to polyoxyethylene ethers of a mixture of high molecular mass saturated fatty alcohols. The "n" indicates the average number of ethylene oxide residues in the polyoxyethylene chain. Ceteareth-12 is a non-toxic surfactant which is frequently used as an emulsifier in the cosmetic industry. The mixture of Cetearyl alcohol and Ceteareth-20 (EMULGADE 1000NI, Cognis Corporation) is a non-ionic, self-emulsifying base commonly used in the production of oil/water creams and lotions.

Disodium Edetate, having the chemical name of disodium (ethylene-dinitrilo) tetra-acetate dihydrate, is also commonly known as the disodium salt of EDTA. The chemical acts as a chelating compound by preventing ingredients from binding to trace elements that may be present.

Excipients and antimicrobial/antiviral ingredients useful in forming the skin protective creams, according to the present invention are described in the following non-limiting example.

EXAMPLE 1

In formulating a batch of a skin protective cream according to the invention, active ingredients and excipients useful in the manufacture of this product, a particularly effective product resulted when ingredients were utilized within the following approximate ranges:

| ACTIVE INGREDIENTS/EXCIPIENT | WT/WT % RANGES |
|---|---|
| Water phase | |
| (1) DEIONIZED WATER | Q.S. |
| (2) EDETATE DISODIUM | 0.01-0.1 |
| (3) BENZALKONIUM CHLORIDE | 0.01-0.25 |
| (4) ZINC OXIDE | 1.0-8.0 |
| (5) GLYCERIN (USP) | 2.0-10.0 |
| Oil Phase | |
| (6) DIMETHICONE 20 | 10.0-20.0 |
| (7) DIMETHICONE 12500 | 3.0-10.0 |
| (8) CETEARYL ALCOHOL and/or CETEARETH-20 | 6.0-10.0 |
| (9) CETEARETH-12 | 0.5-3.0 |
| (10) ANYHDROUS LANOLIN | 0.5-3.0 |
| (11) CETOSTEARYL ALCOHOHL | 1.0-5.0 |
| (12) CETYL ALCOHOL | 1.0-5.0 |

A preferred, albeit non-limiting procedure for manufacture of the formulation comprises the steps of:

Procedure:
1. Heat to 75° C.-Dimethicone 20⁻, Dimethicone 12500, Cetearyl Alcohol and Ceteareth-20 (available as EMULGADE 1000 NI from Cognis), Ceteareth-12 (available as (EUMULGIN B1 from Cognis), Anhydrous Lanolin, Cetostearyl alcohol and Cetyl alcohol. Allow the materials to melt.
2. Dissolve Disodium Edetate in the deionized water (USP).
3. Add Benzalkonium Chloride to Step #2
4. Heat Step #3 to 75-78° C.
5. Disperse the Zinc Oxide in the Glycerin to form a homogeneous dispersion.
6. With high speed mixing, slowly add the materials from Step #4 (Water phase) to the materials from Step #1 (Oil phase). Initiate cooling.
7. When at 60° C.; add the dispersion from Step #5 to the materials from Step #6 (Emulsion).
8. When at 50° C., reduce mixing speed.
9. When at 40° C., further reduce the mixing speed.
10. When at 25° C. stop mixing.

While not wishing to be bound to any particular theory, it is believed that these film forming excipients and active ingredient form a neutral and hydrophobic layer barrier which is also believed to interact with the skin thereby having a stabilizing effect upon the hydrophobic layer, which results in the enhanced persistence of the product. The use of a silicone-containing skin protectant, e.g. Dimethicone 20 and Dimethicone 12500, or a like equivalent, acts in coordination with at least one of the skin protectants compositions as defined in CFR 21 Sec. 347.10, e.g. Zinc Oxide, or others from Table 1, excipients and the film-forming emollients, and melts when contacted with the heat of the body. This in turn forms a physical hydrophobic layer that provides a barrier which appears to inhibit penetration of liquids and sexually transmitted pathogens (viral, bacterial) which are primarily hydrophilic in nature. This property helps protect the user from contamination due to sexual contact with infected individuals.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

All patents and publications mentioned in this specification are indicative of the levels of those skilled in the art to which the invention pertains. All patents and publications are herein incorporated by reference to the same extent as if each individual publication was specifically and individually indicated to be incorporated by reference. It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification. One skilled in the art will readily appreciate that the present invention is well adapted to carry out the objectives and obtain the ends and advantages mentioned, as well as those inherent therein. The excipients and related compounds described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An oil-in-water formulation for the inhibition of the transmission of sexually transmitted diseases, characterized by enhanced skin protective properties consisting of in combination:

(1) a skin protectant composition selected from the group consisting of Allantoin, Aluminum hydroxide gel, Calamine, Cocoa Butter, Cod Liver Oil, Colloidal Oatmeal, Hard Fat, Kaolin, Mineral Oil, Petrolatum, Topical Starch, White Petrolatum, Zinc Acetate, Zinc Carbonate, Zinc Oxide, and mixtures thereof, provided in a skin protecting effective concentration;

(2) a silicone-based skin protectant composition containing at least one silicone-containing excipient provided in a skin protecting effective concentration;

(3) a humectant-excipient, selected from the group consisting of glycerin, anhydrous lanolin and combinations thereof, in the range of about 0.5 to 15.0% wt/wt;

(4) a non-ionic emulsifier selected from the group consisting of cetearyl alcohol, ceteareth-12, ceteareth-20 and mixtures thereof, in the range from about 0.5 to 15.0% w/w;

(5) a chelating compound in the range from about 0.1 to 0.01% w/w;

(6) a quaternary ammonium salt in the range from about 0.01 to 0.25% w/w;

(7) a film-forming emollient in the range from about 1.0 to 10.0% w/w; and (8) water;

wherein contact with the skin results in the in situ formation of a skin protective barrier layer effective in preventing transmission of sexually transmitted diseases.

2. The formulation of claim 1 wherein said skin protectant is zinc oxide.

3. The formulation of claim 1 wherein said silicone-based skin protectant is dimethicone 20.

4. The formulation of claim 1 wherein said silicone-based skin protectant is dimethicone 12500.

5. The formulation of claim 1 wherein said silicone-based skin protectant is a combination of dimethicone 20 and dimethicone 12500.

6. The formulation of claim 1, wherein said film-forming emollient is cetostearyl alcohol.

7. The formulation of claim 1, wherein said film-forming emollient is cetyl alcohol.

8. The formulation of claim 1, wherein said film-forming emollient is a combination of cetostearyl alcohol and cetyl alcohol.

9. The formulation of claim 1, wherein said chelating compound is disodium edetate.

10. The formulation of claim 1, wherein said quaternary ammonium salt is benzalkonium chloride.

11. The formulation of claim 1, wherein said quaternary ammonium salt is alkyltrimethylammonium bromide.

12. The formulation of claim 1, wherein said formulation is in the form of a cream.

13. The formulation of claim 1, wherein said formulation is in the form of a lotion.

* * * * *